(12) United States Patent
Nakagawa (10) Patent No.: US 9,074,964 B2
(45) Date of Patent: Jul. 7, 2015

(54) TRANSMISSION TESTING DEVICE (71) Applicant: MEIDENSHA CORPORATION, Tokyo (JP)

(72) Inventor: Takahiro Nakagawa, Tokyo (JP)

(73) Assignee: MEIDENSHA CORPORATION, Tokyo (JP)

( * ) Notice: Subject to any disclaimer, the term of this patent is extended or adjusted under 35 U.S.C. 154(b) by 0 days.

(21) Appl. No.: 14/373,130

(22) PCT Filed: Jan. 18, 2013

(86) PCT No.: PCT/JP2013/050963
§ 371 (c)(1),
(2) Date: Jul. 18, 2014

(87) PCT Pub. No.: WO2013/111685
PCT Pub. Date: Aug. 1, 2013

(65) Prior Publication Data
US 2014/0360284 A1 Dec. 11, 2014

(30) Foreign Application Priority Data
Jan. 23, 2012 (JP) ................................. 2012-010687

(51) Int. Cl.
*G01L 3/02* (2006.01)
*G01M 13/02* (2006.01)
*G01N 3/02* (2006.01)

(52) U.S. Cl.
CPC ............ *G01M 13/02* (2013.01); *G01M 13/022* (2013.01); *G01N 3/02* (2013.01)

(58) Field of Classification Search
CPC ....... G01M 13/02; G01M 13/022; G01N 3/02
USPC .................................... 73/760, 781, 862.191
See application file for complete search history.

(56) References Cited

U.S. PATENT DOCUMENTS

| | | | | |
|---|---|---|---|---|
| 4,403,504 A | * | 9/1983 | Krage et al. | 73/114.29 |
| 5,085,071 A | * | 2/1992 | Mizushina et al. | 73/115.02 |
| 5,086,271 A | * | 2/1992 | Haill et al. | 324/750.05 |
| 6,612,163 B2 | | 9/2003 | Kamiyama et al. | |
| 2003/0167143 A1 | * | 9/2003 | Turbett et al. | 702/113 |
| 2006/0154759 A1 | * | 7/2006 | Reuschel | 474/8 |

FOREIGN PATENT DOCUMENTS

| | | |
|---|---|---|
| JP | 3-8743 U | 1/1991 |
| JP | 6-51854 U | 7/1994 |
| JP | 2001-221717 A | 8/2001 |
| JP | 2002-5791 A | 1/2002 |

(Continued)

*Primary Examiner* — Max Noori
(74) *Attorney, Agent, or Firm* — Foley & Lardner LLP (57) ABSTRACT

Provision of an intermediate shaft and a torque meter between a test product and a dynamometer in a transmission testing device in which the test product is set in an environmental chamber leads to a long axial length and thereby requires a large floor area for setting, and also causes a twisting of a shaft and leads to a poor rigidity. A hollow spacer is provided between a face plate of the environmental chamber and a test product attachment holder to which the test product is attached. A flange with an H-shape in side view is disposed in the hollow of the spacer. The flange has an end connected to an adaptor flange fixed to the test product, and another end connected to a rotating shaft of the dynamometer via the torque meter.

12 Claims, 9 Drawing Sheets

DIAGRAM SHOWING CONFIGURATION OF TESTING DEVICE
ACCORDING TO PRESENT INVENTION

(56) References Cited

FOREIGN PATENT DOCUMENTS

| | | |
|---|---|---|
| JP | 2002-214081 A | 7/2002 |
| JP | 4010087 B2 | 11/2007 |
| JP | 2007-333475 A | 12/2007 |
| JP | 2008-46006 A | 2/2008 |
| JP | 2012-18137 A | 1/2012 |

* cited by examiner

FIG. 1

DIAGRAM SHOWING CONFIGURATION OF TESTING DEVICE ACCORDING TO PRESENT INVENTION

FIG. 2

DIAGRAM SHOWING PARTIAL CONFIGURATION OF PRESENT INVENTION

FIG. 4

DIAGRAM SHOWING PARTIAL CONFIGURATION OF PRESENT INVENTION

FIG. 5

DIAGRAM SHOWING PARTIAL CONFIGURATION OF PRESENT INVENTION

FIG. 6
DIAGRAM SHOWING PARTIAL CONFIGURATION OF PRESENT INVENTION

FIG. 7
DIAGRAM SHOWING PARTIAL CONFIGURATION OF PRESENT INVENTION

FIG. 8

DIAGRAM SHOWING PARTIAL CONFIGURATION OF PRESENT INVENTION

FIG. 9 DIAGRAM SHOWING CONFIGURATION OF PRESENT INVENTION

FIG. 10

DIAGRAM SHOWING CONFIGURATION OF CONVENTIONAL TRANSMISSION TESTING DEVICE

TRANSMISSION TESTING DEVICE

TECHNICAL FIELD

The present invention relates to a transmission testing device, and particularly to a transmission testing device in which an intermediate shaft for connection between a dynamometer and a test product is removed, and a torque meter is protected accordingly.

BACKGROUND ART

Figure 10:
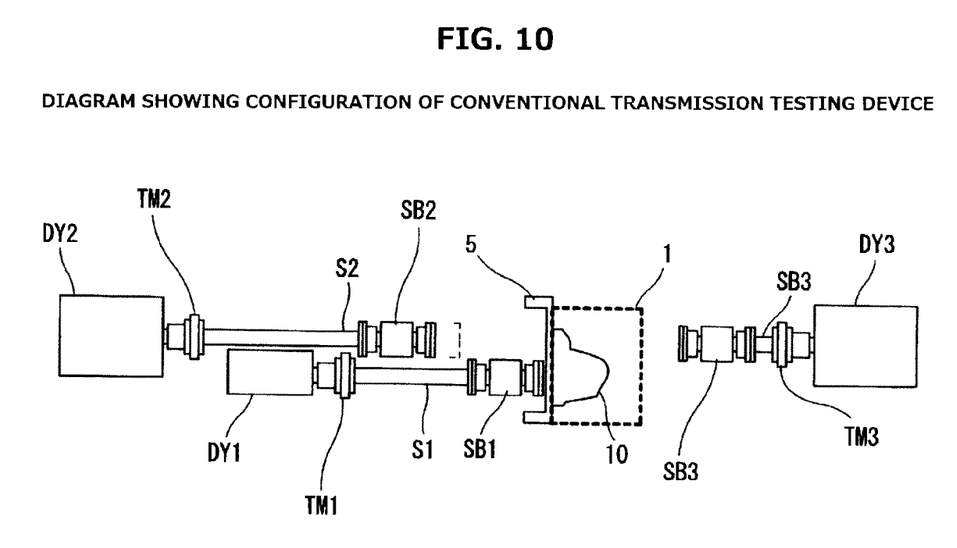
FIG. 10 is a configuration diagram of a conventional transmission testing device.

For a transmission testing device, a test result about a torque converter which is an important component of a transmission has become important among automotive components. Such a transmission testing device is known in a patent document 1 and others. FIG. 10 shows configuration of a transmission testing device as disclosed in patent document 1, wherein 1 denotes an environmental chamber, 10 denotes a test product (a transmission and a torque converter) set in the environmental chamber, Dy1 denotes an input shaft dynamometer, and Dy2, Dy3 denote output shaft dynamometers, wherein each dynamometer is placed and fixed on a bed.

A rotating shaft of the input shaft dynamometer Dy1 is connected to an end of an intermediate shaft S1 through a torque meter TM1. The other end of the intermediate shaft S1 is rotatably supported on an intermediate shaft bearing SB1 and extends through a wall of the environmental chamber 1 and projects into the environmental chamber 1. Each output shaft dynamometer Dy2, Dy3 is connected to the torque meter TM2, TM3 and intermediate shaft bearing SB2, SB3, and intermediate shaft S2, 53, and connected to an output shaft of the test product 10.

Patent Document 1: Japanese Patent No. 4010087

DISCLOSURE OF THE INVENTION

An environmental test is performed in the environmental chamber 1 in which the test product 10 is set, at low to high temperatures, for example, in a temperature range from −40° C. to 150° C. Accordingly, the difference in temperature between the side of dynamometer Dy1 and the environmental chamber 1 causes an error in the horizontal axis of the intermediate shaft S1. In order to prevent this error, a heater is attached to adjust the temperature to prevent the occurrence of an error in patent document 1.

In recent years, various transmission testing devices have been developed, and it is desired to enhance the functionality and accuracy in measurement in performance evaluation tests for a test product, and downsize the facility.

In consideration of the foregoing requests, it is an object of the present invention to provide a transmission testing device in which the accuracy of measurement can be enhanced, and the downsizing of the facility can be achieved.

According to one aspect of the present invention, a transmission testing device for testing a test product at a temperature inside of an environmental chamber, wherein the test product is set in the environmental chamber and connected to an input shaft dynamometer through a torque meter arranged out of the environmental chamber, wherein: the test product is arranged to face a hole formed in a face plate, and is fixed to the face plate, and is attached to a test product attachment holder through the face plate, wherein the test product attachment holder is disposed outside of the environmental chamber; the test product attachment holder includes an opened side surface, and a second side surface opposite to the opened side surface, wherein the second side surface is formed with a hole having a box-shape; attachment of the test product to the test product attachment holder is implemented by fixing the face plate under a condition where the hole of the face plate and the hole of the test product attachment holder face each other, and arranging a flange in a hollow formed in the test product attachment holder for connection between the test product and the input shaft dynamometer, and connecting a first end of the flange to an adapter flange of the test product, and connecting a second end of the flange to a rotating shaft of the input shaft dynamometer through the torque meter; and a thermal insulation wall is provided at a test-product-fixing-side inner wall of the test product attachment holder, for suppressing thermal conduction from the environmental chamber.

According to a further aspect of the present invention, the flange is provided with a thermal radiation flange at a shaft thereof, for preventing conduction of cold atmosphere and hot atmosphere from the environmental chamber to the torque meter through the flange.

According to another aspect of the present invention, the thermal insulation wall is composed of separate parts; and the hole of the test product attachment holder is covered by an insulation plate after coupling between the test product and the flange.

According to a further aspect of the present invention, the hollow of the test product attachment holder is connected to an air duct such that air is sent into the hollow through the air duct.

According to another aspect of the present invention, a transmission testing device for testing a test product at a temperature inside of an environmental chamber, wherein the test product is set in the environmental chamber and connected to an input shaft dynamometer through a torque meter arranged out of the environmental chamber, wherein: the test product is arranged to face a hole formed in a face plate, and is fixed to the face plate; a test product attachment holder is disposed outside of the environmental chamber, and is formed with a hole in a position facing a position of the test product, wherein the hole of test product attachment holder faces the hole of the face plate; a hollow spacer is disposed between the hole of the test product and the hole of the test product attachment holder, wherein the test product is attached to the test product attachment holder through the face plate; and a flange is located in a hollow of the spacer, having an H-shape in side view, wherein the flange has a first end connected to an adapter flange fixed to the test product, and a second end connected to a rotating shaft of the input shaft dynamometer through the torque meter.

According to a further aspect of the present invention, the transmission testing device further comprises a thermal insulation wall in the hollow of the spacer, for preventing conduction of cold atmosphere and hot atmosphere from the environmental chamber to the torque meter.

According to another aspect of the present invention, the transmission testing device further comprises: a constant temperature chamber provided in the hollow of the spacer between the thermal insulation wall and the torque meter; and a temperature sensor disposed in the constant temperature chamber; wherein temperature of the constant temperature chamber is controlled based on a sensing signal from the temperature sensor.

According to a further aspect of the present invention, the flange is provided with a thermal radiation flange at a shaft thereof, for preventing conduction of cold atmosphere and hot atmosphere from the environmental chamber to the torque meter through the flange.

According to another aspect of the present invention, the thermal insulation wall is composed of separate parts; and the hole of the test product attachment holder is covered by an insulation plate after coupling between the test product and the flange.

BEST MODE(S) FOR CARRYING OUT THE INVENTION

According to the present invention, in a testing device for testing a test product at a temperature inside of an environmental chamber, a hollow is defined between a face plate of the environmental chamber and a test product attachment holder to which the test product is attached. A flange is located in the hollow, having an H-shape in side view. The flange has a first end connected to an adapter flange fixed to the test product, and a second end connected to a rotating shaft of an input shaft dynamometer through a torque meter. As necessary, the hollow is provided therein with a thermal insulation wall, or a thermal insulation wall and a constant temperature chamber. The following describes the present invention with reference to embodiments.

Figures 1, 2:
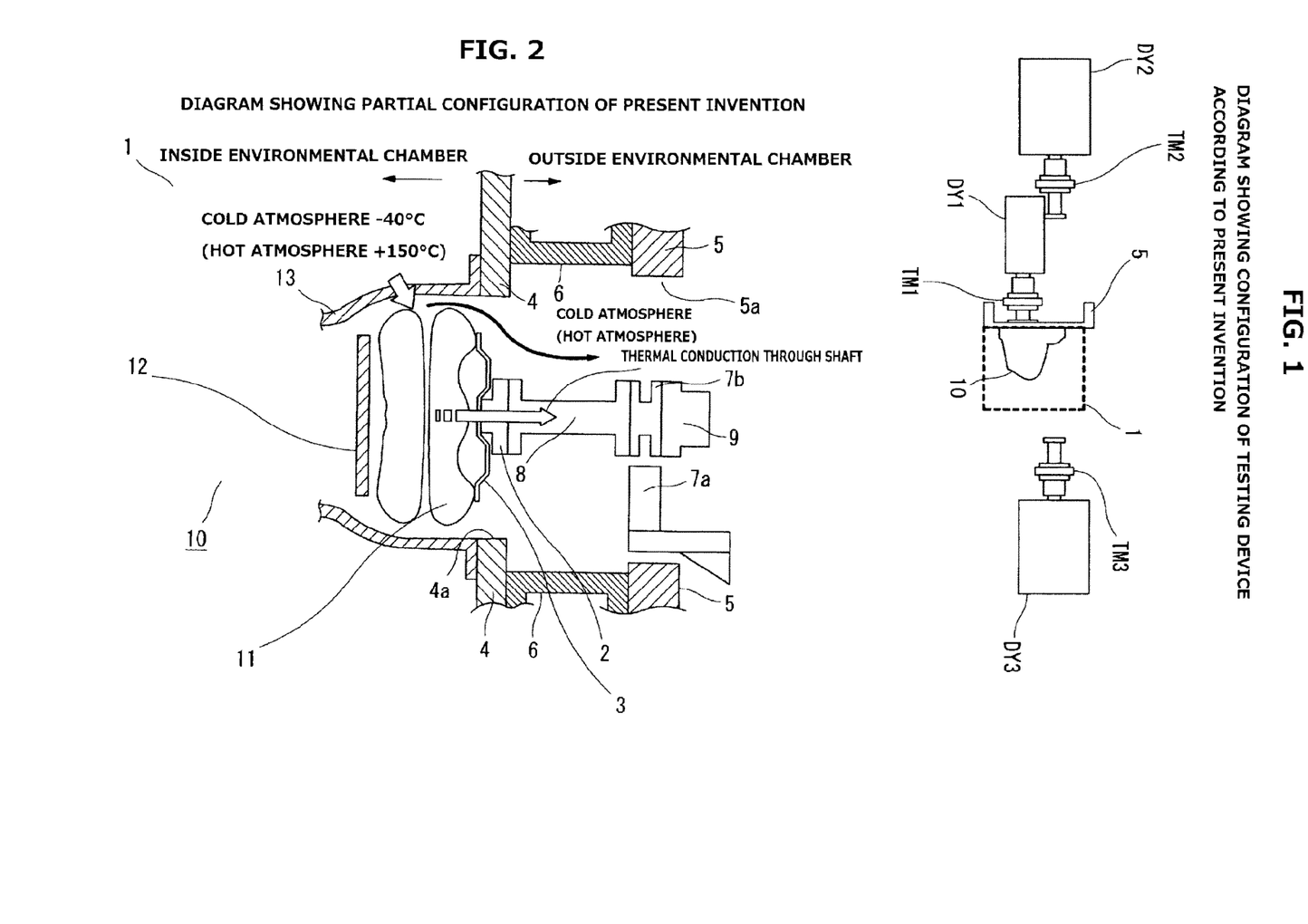
FIG. 1 is a configuration diagram of a transmission testing device according to an embodiment of the present invention.
FIG. 2 is a partially enlarged diagram showing the embodiment of the present invention.

FIG. 1 is a configuration diagram showing an embodiment of the present invention, wherein components identical or corresponding to those in FIG. 10 are given the same reference signs. Namely, in the present invention, an intermediate shaft S1 and an intermediate shaft bearing SB1, which are connected to a dynamometer Dy1, are removed.

FIG. 2 is an enlarged diagram showing a place where the dynamometer and the test product are connected. A test product 10 includes a torque converter 11 and a transmission 12, and is covered by a cover 13 made of metal, and is arranged in an environmental chamber 1. The test product 10 is fixed to a face plate 4 through the cover 13. The face plate 4 is formed with an opening 4a. An adapter flange 2 and a drive plate 3 which constitute an input shaft to the torque converter 11 are located close to the opening 4a.

A test product attachment holder 5 is formed with an opening 5a at a position facing the opening 4a of the face plate 4. Cold or hot atmosphere is exhausted from the environmental chamber through the opening 5a to the outside of the device. A torque meter 7 includes a signal-receiving part (henceforth referred to as stator part) 7a at a fixed portion, wherein the signal-receiving part 7a receives a sensed torque signal. A spacer 6 has a hollow having a larger diameter than the opening 4a of the face plate 4 and a predetermined length, and is disposed between the face plate 4 and the test product attachment holder 5. A flange 8 for adaption to the environmental chamber has an H-shape in side view, and has a length substantially equal to the length of the spacer 6, and has a first end fixed to the adapter flange 2, and a second end fixed to a rotor part 7b of the torque meter 7. The other end of the rotor part 7b is connected to a rotating shaft of the input shaft dynamometer Dy1 through a coupling 9.

In the configuration described above, the inside of the environmental chamber 1 is set under a predetermined environment, and the dynamometer is driven instead of an engine, a torque is transmitted to the torque converter 11 through the coupling 9, the rotor part 7b of the torque meter, the flange 8, the adapter flange 2, and the drive plate 3. A test is performed for evaluating the performance and endurance of the torque converter under a specific condition. In this configuration, the dynamometer and the torque converter are connected to each other only by the flange 8 and the coupling 9, with no intermediate shaft as in the conventional configuration.

According to this embodiment, an intermediate shaft S2 of an output shaft dynamometer Dy2 can be also shortened, because the intermediate shaft for connection between the test product in the environmental chamber 1 and the input shaft dynamometer as in the conventional configuration is removed. This allows to significantly reduce the size of the entire testing device in the lateral axis direction and thereby reduce the area where the testing device is set. Moreover, the removal of the intermediate shaft serves to prevent the occurrence of a twisting of the connection shaft between the test product and the dynamometer and thereby enhance the rigidity, and heighten the resonance frequency and thereby enhance the responsiveness. In order to perform a vibration control of the input torque, it is necessary to enhance the rigidity. The resonance frequency is conventionally about 200 Hz, but is raised by the present invention to about 290-320 Hz which was confirmed experimentally.

Incidentally, it is conceivable that the removal of the conventional intermediate shaft causes the position of the torque meter to become close to the environmental chamber, and may cause the torque meter to be damaged thermally. However, in this embodiment, the position of the torque meter 7 is between the flange 8 and the coupling 9 coupling the input shaft dynamometer, and is at the opening 5a of the test product attachment holder 5 wherein the opening 5a is located in a space in contact with air in an ordinary temperature space. Accordingly, even without the intermediate shaft, the temperature of the torque meter 7 is relatively little influenced by the temperature in the environmental chamber 1, and is suppressed from rising.

Figure 3:
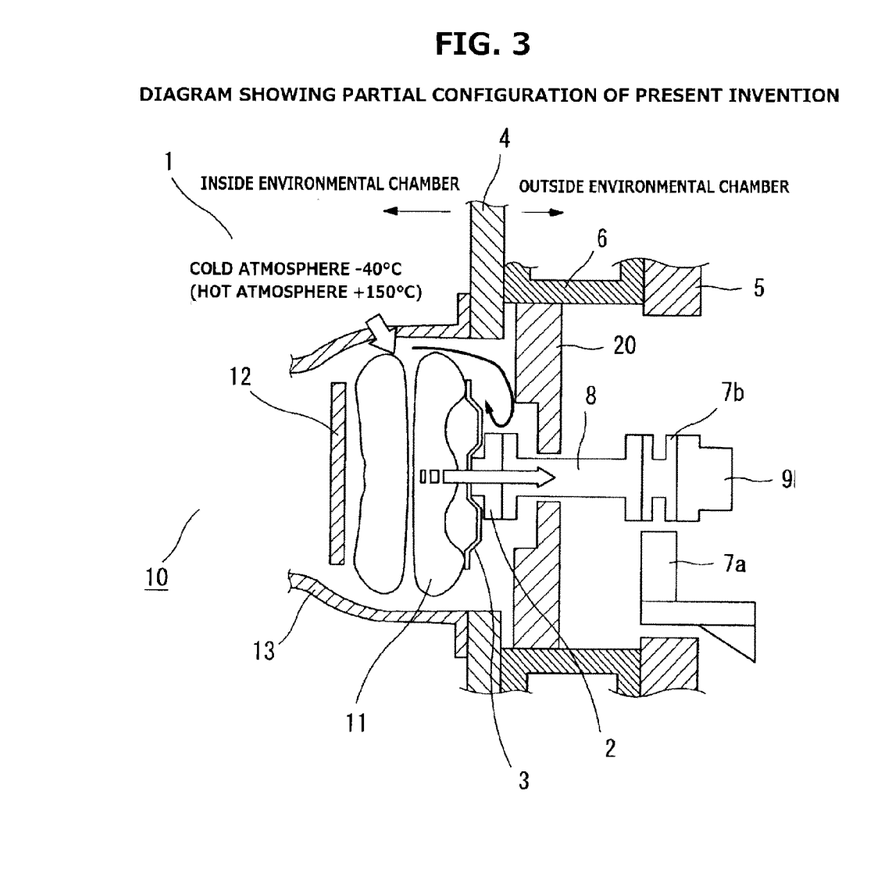
FIG. 3 is a partially enlarged diagram showing another embodiment of the present invention.

FIG. 3 is a partial diagram showing a second embodiment, which is different from the first embodiment in that a thermal insulation wall 20 is provided in the hollow of the spacer 6. The environmental test is performed at a temperature range from −40° C. Accordingly, as indicated by an arrow in FIG. 2, especially during testing at low temperature or at high temperature, cold or hot atmosphere in the environmental chamber 1 may enter the hollow of the spacer 6 through the metal cover 13, and thermal conduction through the torque converter 11, the adapter flange 2, the flange 8, and the torque meter 7 may occur such that high or low temperature may cause a damage in the torque meter and an error in the sensed torque value.

In the second embodiment shown in FIG. 3, the thermal insulation wall 20 is provided close to the connection point between the face plate 4 and the spacer 6 for protecting the torque meter 7 from cold or hot atmosphere. Accordingly, as indicated by an arrow, cold or hot atmosphere entering the hollow of the spacer 6 is blocked by the thermal insulation wall 20 from flowing toward the torque meter 7, preventing the occurrence of a damage in the torque meter and an error in the sensing.

According to this embodiment, in addition to the effects described with respect to the first embodiment, it is further possible to protect the torque meter and prevent the occurrence of an error in the sensing value due to temperature. Thermal expansion of the flange 8, the coupling 9, and others, is prevented, so that axis deviation of those components at the coupling point is prevented and the occurrence of a vibration is suppressed.

Figure 4:
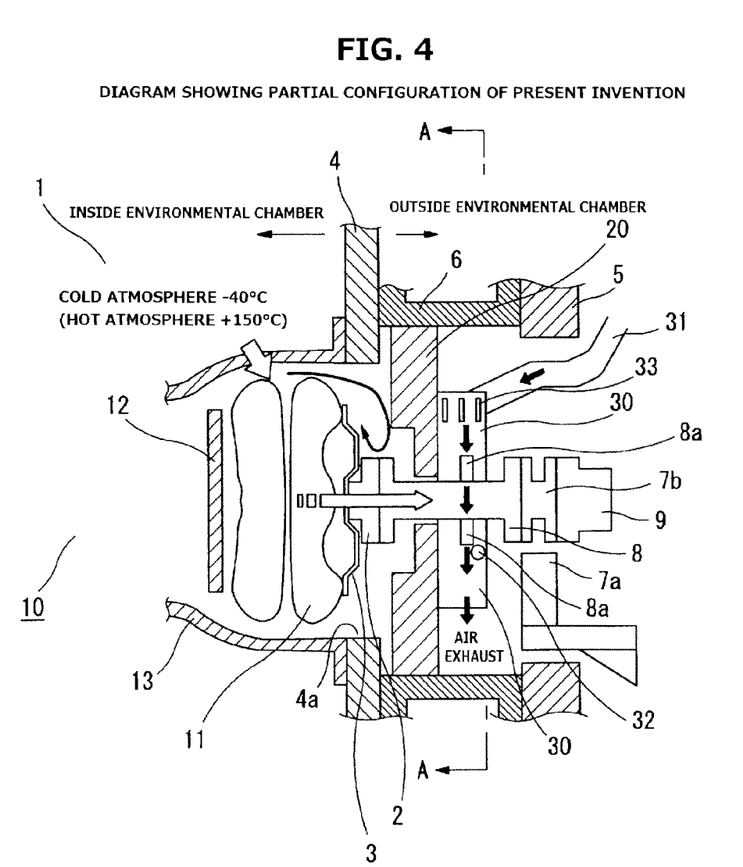
FIG. 4 is a partially enlarged diagram showing another embodiment of the present invention.

FIG. 4 is a partial diagram showing a third embodiment, in which the flange 8 in the hollow of the spacer 6 is provided with a thermal radiation flange 8a, and a constant temperature chamber 30 is provided to surround the thermal radiation flange 8a, so that heat transmitted through the flange 8 is radiated through an increased area of the thermal radiation flange 8a, and is forced to dissipate by the constant temperature chamber 30. The other configuration is the same as in the second embodiment. It is possible to enhance the heat dissipating effect as compared to the case of FIG. 3 only with the thermal radiation flange 8a without the constant temperature chamber 30.

The constant temperature chamber 30 is configured to surround the flange 8 and the thermal radiation flange 8a, and is connected to an air duct 31, and is formed with an air exhaust opening. A temperature sensor 32 and a heater 33 are provided at arbitrary positions in the constant temperature chamber 30, and the air duct 31 is connected to a blower. A temperature signal obtained by the temperature sensor 32 is sent to an operation board not shown, and a control signal is outputted to the heater 33 and the blower.

In general, the torque meter 7 is provided therein with a temperature sensor, which is used to control the blower or an air conditioner. In such a case, the temperature sensor may be omitted, or the temperature sensor shown in FIG. 4 is used as a sensor for redundant protection.

In the present embodiment, when the test product 10 is tested at high temperature, hot atmosphere heated through the cover 13 is blocked by the thermal insulation wall 20 as indicated by an arrow in FIG. 4, and the heat transmitted through the torque converter 11, the drive plate 3, the adapter flange 2, and the flange 8 is radiated by the thermal radiation flange 8a, and is dissipated by suction of air in the constant temperature chamber 30 to prevent thermal conduction to the torque meter.

When the environmental test is performed at high temperature, the blower is driven. The amount of heat exchange at a heat dissipation area of each heat exchange area is calculated beforehand, and the amount of suction of air is controlled based on the temperature signal obtained by the temperature sensor 32. This allows to control the temperature of the constant temperature chamber 30 at an arbitrary set temperature. When the environmental test is performed at low temperature, the temperature of the constant temperature chamber 30 can be controlled to rise to an arbitrary set temperature by controlling the heater 33 based on the sensing signal obtained by the temperature sensor 32.

According to the present embodiment, it is possible to control the temperature of the neighborhood of the torque meter within a predetermined temperature range, so that protection of the torque meter is further ensured and accurate measurement of the torque can be achieved.

Assembling of the testing device configured as described above is implemented by attaching the adapter flange 2 to the test product 10, and fixing the flange 8 to the adapter flange 2, and thereafter attaching the thermal insulation wall 20. At that time, it is necessary to study the attachment of the thermal insulation wall 20 that is set in the hollow of the spacer for preventing thermal conduction of cold or hot atmosphere to the torque meter 7. Moreover, it is desired to simply attach the thermal insulation wall 20.

According to the present invention, since the flange 8 is used while the conventional intermediate shaft is removed, flange portions are formed at ends of the shaft of the flange 8, and have larger diameters than the shaft. In FIG. 4, the thermal radiation flange 8a is further provided so that when the thermal insulation wall 20 is inserted from the torque meter connection side, it is necessary to form the thermal insulation wall 20 with a hole whose diameter is larger than that of the flange portion and the thermal radiation flange 8a. In such a case, cold or hot atmosphere flows toward the torque meter 7 through the hole, reducing the effect of the provision of the thermal insulation wall 20.

Figure 5:
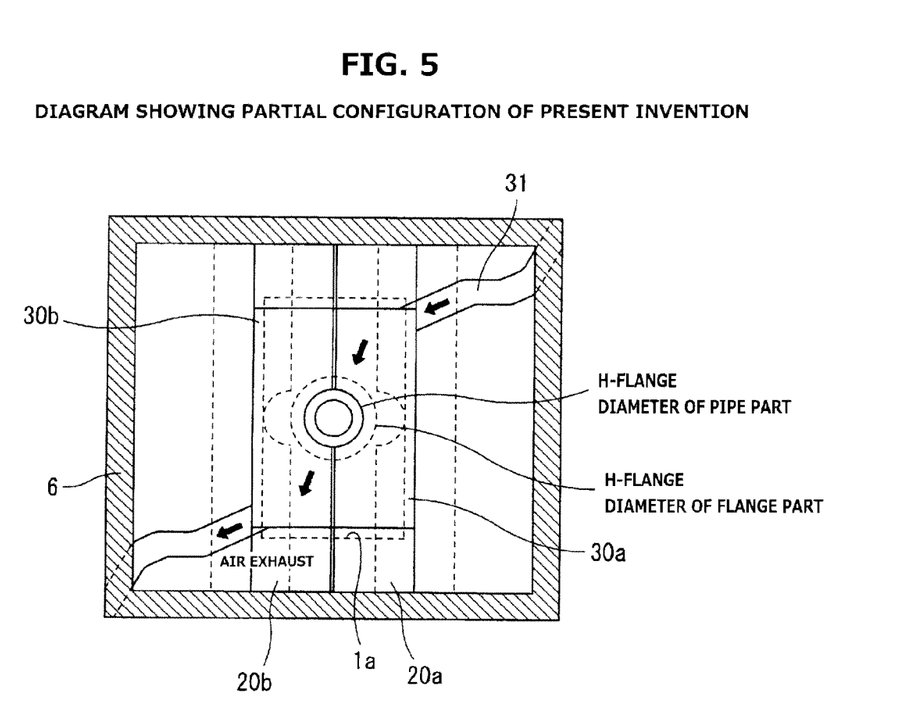
FIG. 5 is a sectional view taken along a line A-A in FIG. 4, showing the other embodiment of the present invention.

FIG. 5 is a configuration diagram for solving that problem, taken along a line A-A in FIG. 4. Specifically, the thermal insulation wall 20 is separated at the neighborhood of the axis of the flange 8 into separate thermal insulation walls 20a, 20b which are configured to laterally slide along the wall surface of the spacer 6. In the embodiment shown in FIG. 5, the constant temperature chamber is also composed of separate parts as well as the thermal insulation wall 20, and the separate parts are made to laterally slide and engage and sandwich the flange 8 and is coupled with each other close to the axis of the flange 8.

According to the present embodiment, it is possible to make the assembling easy, and allow the diameter of the hole formed substantially at the central position of the thermal insulation wall 20 (and the diameter of the hole formed substantially at the central position of the constant temperature chamber 30, if any) to be only slightly larger than the diameter of the shaft of the rotating shaft of the flange 8, and suppress thermal conduction of cold or hot atmosphere, and protect the torque meter, and prevent the occurrence of an error in the sensed temperature value, and thereby perform accurate torque sensing.

Figure 6:
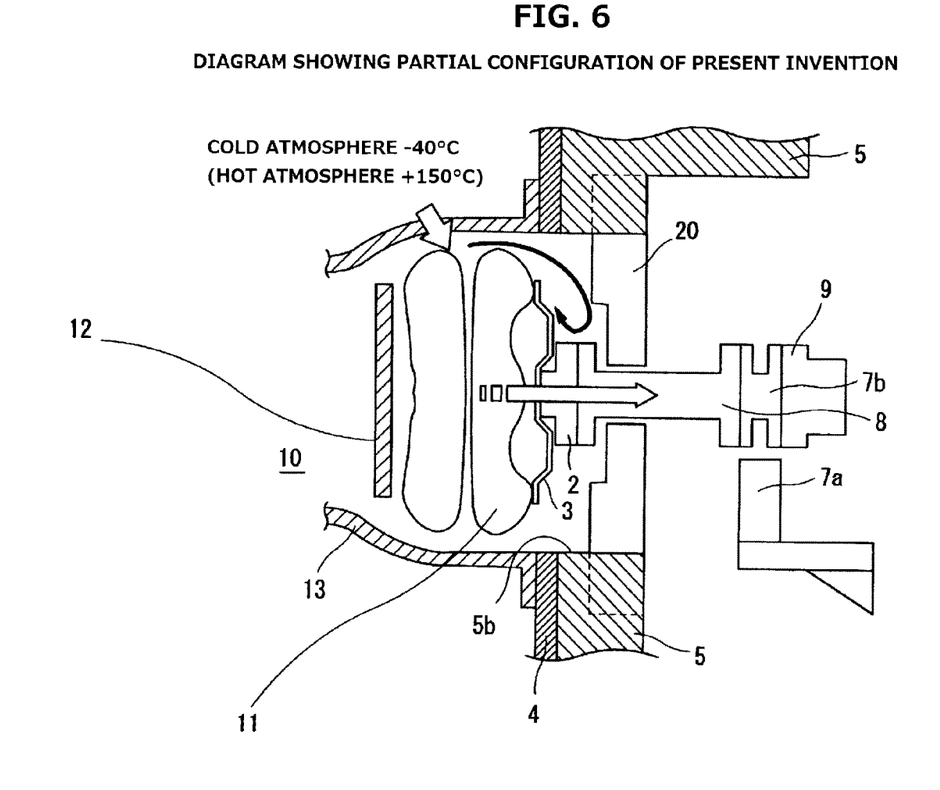
FIG. 6 is a perspective diagram showing another embodiment of the present invention.

FIG. 6 is a partial diagram showing a fifth embodiment, which is different from the first embodiment shown in FIG. 2 in that the spacer 6 is removed, and the test product 10 is attached to the test product attachment holder 5 through the face plate 4. The test product attachment holder 5 is formed to have a box-shape, and has an opening 5b at the side attached to the test product 10, and is opened at a side opposite to the opening 5b. The length from the opened place and the opening 5b is equal to about the length of the spacer 6 shown in FIG. 2. The thermal insulation wall 20 made of an insulation material such as urethane is provided at the inner wall of the test product attachment holder 5 closer to the opening 5b.

In the fifth embodiment shown in FIG. 6, the thermal insulation wall 20 is provided close to the connection point between the test product 10 and the test product attachment holder 5 for protecting the torque meter 7 from cold or hot atmosphere. Accordingly, as indicated by an arrow, cold or hot atmosphere entering the hollow of the test product attachment holder 5 is blocked by the thermal insulation wall 20 from flowing toward the torque meter 7, preventing the occurrence of a damage in the torque meter due to cold or hot atmosphere from the environmental chamber 1. Even when the torque meter is not damaged, it suppresses an error in sensing of the torque meter due to a temperature drift.

According to this embodiment, in addition to the effects described with respect to the first embodiment, it is further possible to protect the torque meter and prevent the occurrence of an error in the sensing value due to temperature. Thermal expansion of the flange 8, the coupling 9, and others, is prevented, so that axis deviation of those components at the coupling point is prevented and the occurrence of a vibration is suppressed.

Figure 7:
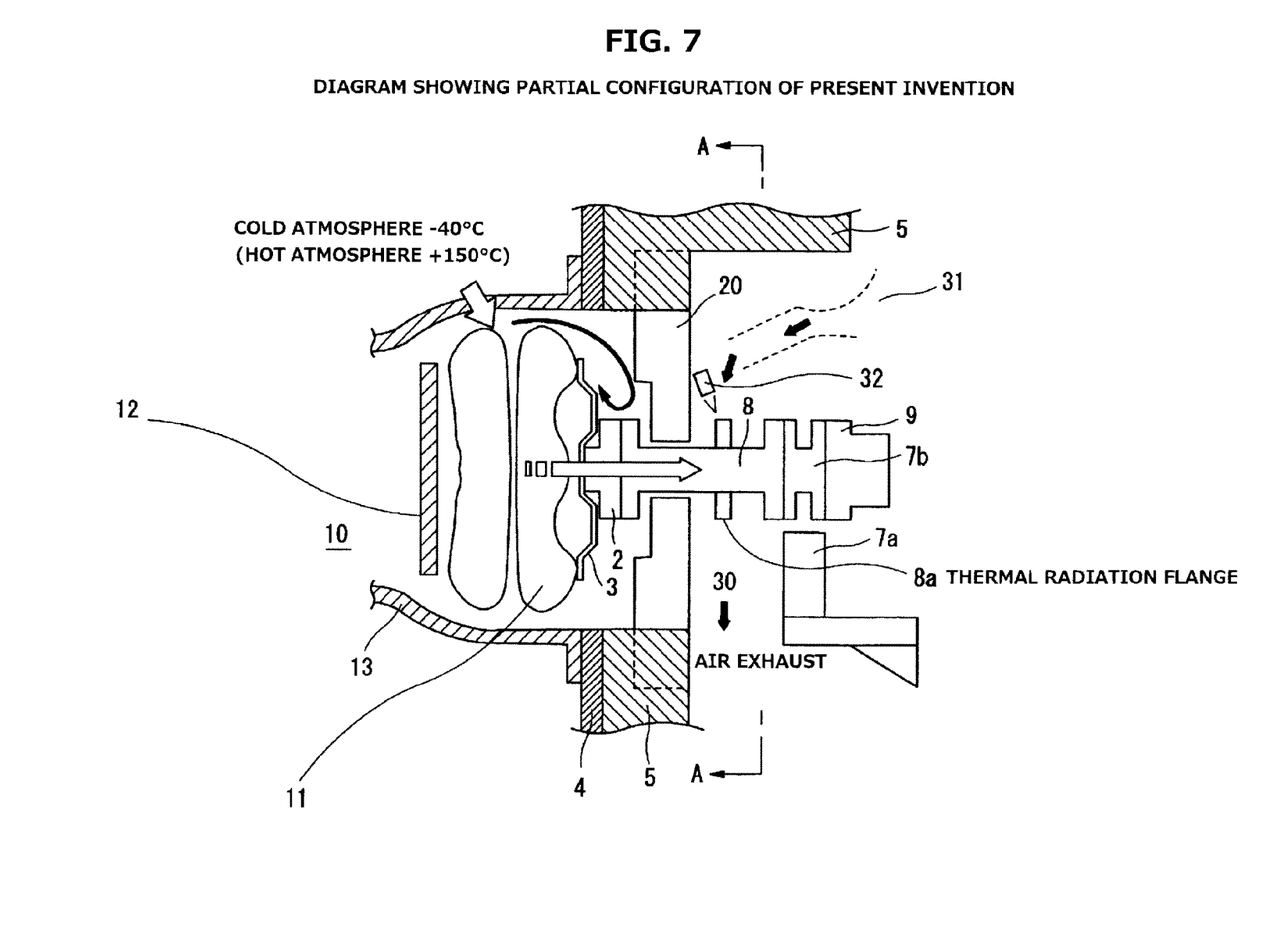
FIG. 7 is a partially enlarged diagram showing another embodiment of the present invention.

FIG. 7 is a partial diagram showing a sixth embodiment, in which the flange 8 is arranged in the hollow of the test product attachment holder 5 and is formed with the thermal radiation flange 8*a*. One end of the air duct 31 is directed to the thermal radiation flange 8*a*, and the other end of the air duct 31 is connected to an air conditioner not shown. Cold or hot air is blown from the air conditioner, depending on the temperature in the environmental chamber. Accordingly, the inside of the box-shaped test product attachment holder 5 is formed with the constant temperature chamber section 30, and the constant temperature chamber section 30 promotes dissipation of the heat transmitted through the flange 8 and the thermal radiation flange 8*a*.

In the constant temperature chamber section 30, an air exhaust path is formed at a position between the thermal insulation wall 20 and the fixed side including the signal-receiving part 7*a* of the torque meter. However, the constant temperature chamber section 30 may be configured to surround the flange 8 and the thermal radiation flange 8*a* and connected to the air duct 31, and part of the constant temperature chamber section 30 may be formed with an air exhaust outlet. The other configuration is the same as in the fifth embodiment shown in FIG. 6. Although the constant temperature chamber section 30 is formed in FIG. 7, the constant temperature chamber section 30 may be omitted. The provision of the thermal radiation flange 8*a* solely serves to enhance the heat dissipating effect.

Air is blown to the constant temperature chamber section 30 through the air duct 31. The temperature sensor 32 is provided at an arbitrary position in the constant temperature chamber 30. A temperature signal obtained by the temperature sensor 32 is sent to an operation board not shown, and is used to output a control signal to the air conditioner.

In the present embodiment, when the test product 10 is tested at high temperature, hot atmosphere heated through the cover 13 is blocked by the thermal insulation wall 20 as indicated by an arrow in FIG. 4, and the heat transmitted through the torque converter 11, the drive plate 3, the adapter flange 2, and the flange 8 is radiated by the thermal radiation flange 8*a*, and is dissipated by suction of air in the constant temperature chamber 30 to prevent thermal conduction to the torque meter 7.

According to the present embodiment, it is possible to control the temperature of the neighborhood of the torque meter within a predetermined temperature range, so that protection of the torque meter is further ensured and accurate measurement of the torque can be achieved.

Assembling of the testing device configured as described above is implemented by attaching the adapter flange 2 to the test product 10, and fixing to the adapter flange 2 the flange 8 having the H-shape in side view, and thereafter attaching the thermal insulation wall 20. At that time, it is necessary to study the attachment of the thermal insulation wall 20 that is set in the hollow of the test product attachment holder 5 for preventing thermal conduction of cold or hot atmosphere to the torque meter 7. Moreover, it is desired to simply attach the thermal insulation wall 20.

According to the present invention, since the flange 8 is used while the conventional intermediate shaft is removed, flange portions are formed at ends of the shaft of the flange 8, and have larger diameters than the shaft. In FIG. 7, the thermal radiation flange 8*a* is further provided so that when the thermal insulation wall 20 is inserted from the torque meter connection side, it is necessary to form the thermal insulation wall 20 with a hole whose diameter is larger than that of the flange portion and the thermal radiation flange 8*a*. In such a case, cold or hot atmosphere flows toward the torque meter 7 through the hole, reducing the effect of the provision of the thermal insulation wall 20.

Figure 8:
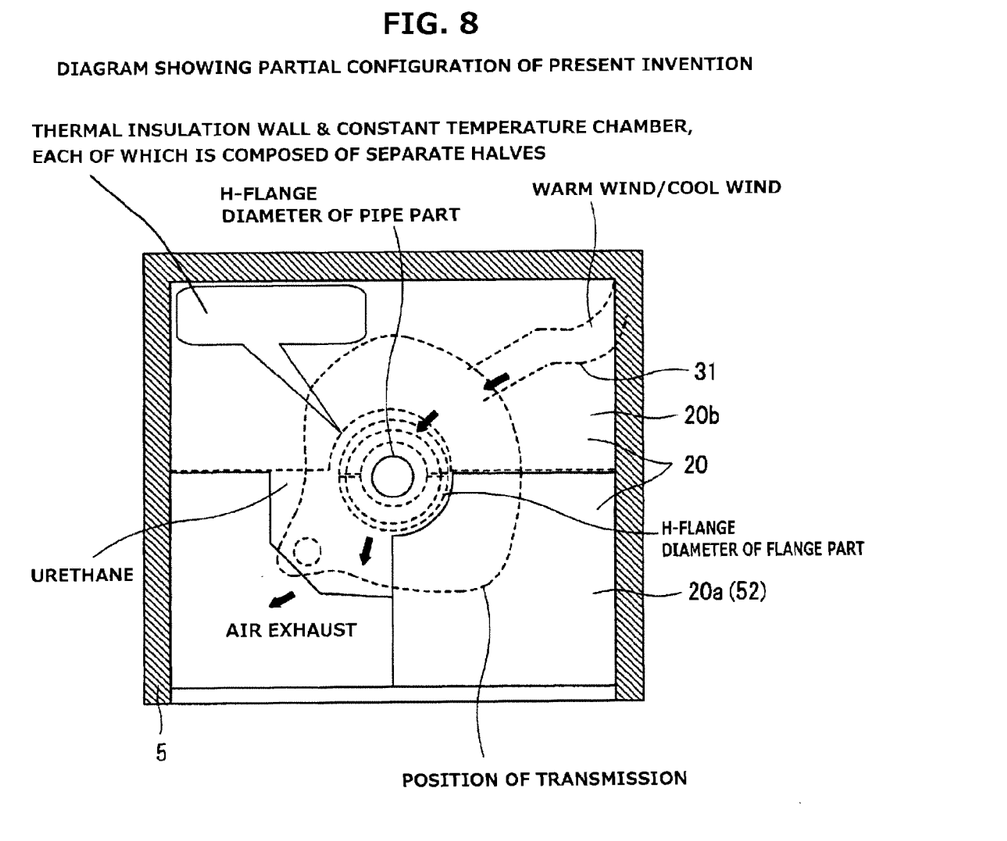
FIG. 8 is a sectional diagram taken along a line A-A in FIG. 7, showing the other embodiment of the present invention.

FIG. 8 is a view taken along a line A-A in FIG. 7, showing that assembling of the testing device shown in FIG. 7 is simplified. Specifically, the thermal insulation wall 20 is separated at the neighborhood of the axis of the flange 8 into separate thermal insulation walls 20*a*, 20*b* which are configured to laterally slide along the wall surface of the spacer 6. In the embodiment shown in FIG. 8, the constant temperature chamber is also composed of separate parts as well as the thermal insulation wall 20, and the separate parts are made to laterally slide and engage and sandwich the flange 8 and is coupled with each other close to the axis of the flange 8.

According to the present embodiment, it is possible to make the assembling easy, and allow the diameter of the hole formed substantially at the central position of the thermal insulation wall 20 (and the diameter of the hole formed substantially at the central position of the constant temperature chamber 30, if any) to be only slightly larger than the diameter of the shaft of the rotating shaft of the flange 8, and suppress thermal conduction of cold or hot atmosphere, and protect the torque meter, and prevent the occurrence of an error in the sensed temperature value, and thereby perform accurate torque sensing.

Figure 9:
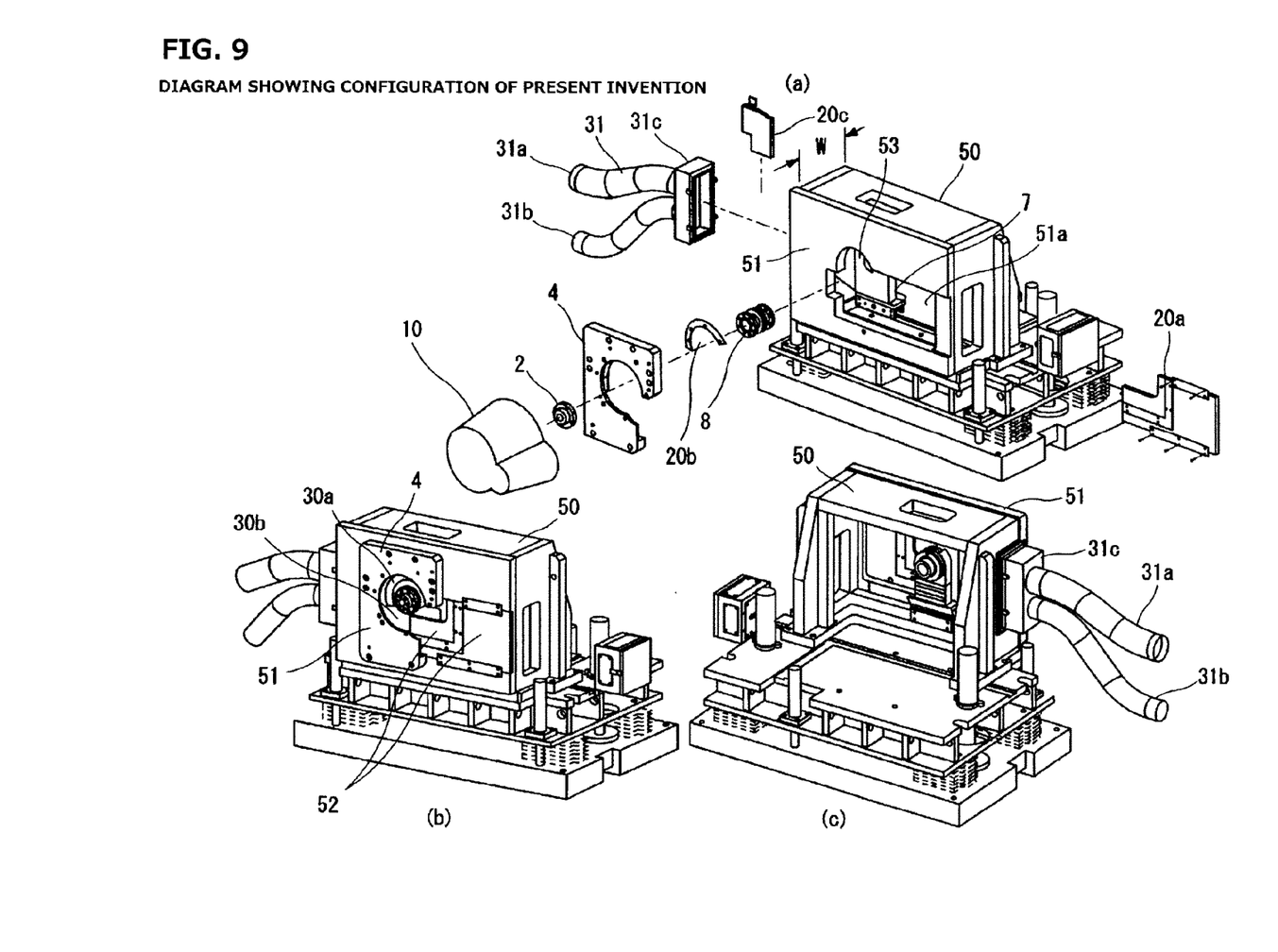
FIG. 9 is a perspective diagram showing another embodiment of the present invention.

FIG. 9 shows an embodiment in which the thermal insulation wall 20 is composed of three separate parts, and the test product attachment holder is formed to have a box-shape, and the flange 8 having an H-shape is disposed in the box-shaped hollow of the test product attachment holder. In FIG. 9, (a) is a perspective view showing a component configuration, (b) is a perspective view showing a condition in which components are attached, as viewed from the test product attachment side, and (c) is a component assembled condition diagram of the test product attachment holder as viewed from the side of the dynamometer Dy1.

In FIG. 9, a test product attachment holder 50 has a box-shape, and has a hollow having a width W. The width W of the hollow is about twice the length of the spacer 6 shown in FIG. 2. When a front face side is assumed as the side where the test product 10 is attached to the test product attachment holder 50, a front face plate 51 is formed with a cutout 51*a* (opening 5*a* in FIG. 2) extending laterally. The test product 10 is fixed to a part of the front face plate 51 through the face plate 4. The thermal insulation wall 20 is separated into three parts 20*a*, 20*b*, 20*c*. The thermal insulation wall 20*a* covers the cutout 51*a* which is not covered by the face plate 4, and thereby blocks cold or hot atmosphere, and for example, is configured to slide along the cutout 51*a* in the lateral direction.

The rear side of the test product attachment holder 50 is opened, where the torque meter 7 is set along the horizontal axis of the flange 8. The side face of the test product attachment holder 50 is formed with an opening to which a connection box 31*c* of the air duct 31 is attached. The air duct 31 includes a hose 31*a* connected to an air blowing device and a hose 31*b* connected to a hot wind generating device, and provides a wind through the connection box 31*c* into the box shape of the test product attachment holder 50 serving as a constant temperature chamber. A windshield plate 52 blocks cold or hot atmosphere from the environmental chamber, and a windshield plate 53 is provided for the torque meter.

In the present embodiment, assembling is performed as follows. The torque meter 7 and the windshield plate 52 are attached to the test product attachment holder 50 beforehand. Under this condition, as shown in FIG. 9 (a), the flange 8 is located in the box shape and one end of the flange 8 is connected to the rotor part of the torque meter 7, under a condition where the thermal insulation wall 20a is detached. Next, the face plate 4 to which the separate thermal insulation wall 20b is fixed is attached to the front face plate 51, and then the flange 8 and the adapter flange 2 and the test product 10 are coupled together, and the other separate thermal insulation wall 20c is attached to the front face plate 51. Thereafter, the cutout 51a is covered by the thermal insulation wall 20a, and the connection box 31c of the air duct is attached, leading to the condition of FIG. 9 (b) (in which the test product 10 is detached).

According to the present embodiment, it is possible to make the assembling easy, and suppress thermal conduction of cold or hot atmosphere, and protect the torque meter, and prevent the occurrence of an error in the sensed temperature value, and thereby perform accurate torque sensing.

As described above, according to the present invention, the removal of the conventional intermediate shaft serves to reduce the setting area, and prevent a twisting of the connection shaft between the test product and the dynamometer, and enhance the rigidity, and enhance the responsiveness. The provision of the thermal insulation wall or the thermal insulation wall and the constant temperature chamber section in the hollow of the spacer, serves to protect the torque meter, and suppress the temperature error and thereby achieve accurate torque sensing, during environmental testing.

The invention claimed is:

1. A transmission testing device for testing a test product at a temperature inside of an environmental chamber, wherein the test product is set in the environmental chamber and connected to an input shaft dynamometer through a torque meter arranged out of the environmental chamber, wherein:
   the test product is arranged to face a hole formed in a face plate, and is fixed to the face plate, and is attached to a test product attachment holder through the face plate, wherein the test product attachment holder is disposed outside of the environmental chamber;
   the test product attachment holder includes an opened side surface, and a second side surface opposite to the opened side surface, wherein the second side surface is formed with a hole having a box-shape;
   attachment of the test product to the test product attachment holder is implemented by fixing the face plate under a condition where the hole of the face plate and the hole of the test product attachment holder face each other, and arranging a flange in a hollow formed in the test product attachment holder for connection between the test product and the input shaft dynamometer, and connecting a first end of the flange to an adapter flange of the test product, and connecting a second end of the flange to a rotating shaft of the input shaft dynamometer through the torque meter; and
   a thermal insulation wall is provided at a test-product-fixing-side inner wall of the test product attachment holder, for suppressing thermal conduction from the environmental chamber.

2. The transmission testing device as claimed in claim 1, wherein the flange is provided with a thermal radiation flange at a shaft thereof, for preventing conduction of cold atmosphere and hot atmosphere from the environmental chamber to the torque meter through the flange.

3. The transmission testing device as claimed in claim 1, wherein:
   the thermal insulation wall is composed of separate parts; and
   the hole of the test product attachment holder is covered by an insulation plate after coupling between the test product and the flange.

4. The transmission testing device as claimed in claim 1, wherein the hollow of the test product attachment holder is connected to an air duct such that air is sent into the hollow through the air duct.

5. A transmission testing device for testing a test product at a temperature inside of an environmental chamber, wherein the test product is set in the environmental chamber and connected to an input shaft dynamometer through a torque meter arranged out of the environmental chamber, wherein:
   the test product is arranged to face a hole formed in a face plate, and is fixed to the face plate;
   a test product attachment holder is disposed outside of the environmental chamber, and is formed with a hole in a position facing a position of the test product, wherein the hole of test product attachment holder faces the hole of the face plate;
   a hollow spacer is disposed between the hole of the test product and the hole of the test product attachment holder, wherein the test product is attached to the test product attachment holder through the face plate; and
   a flange is located in a hollow of the spacer, having an H-shape in side view, wherein the flange has a first end connected to an adapter flange fixed to the test product, and a second end connected to a rotating shaft of the input shaft dynamometer through the torque meter.

6. The transmission testing device as claimed in claim 5, further comprising a thermal insulation wall in the hollow of the spacer, for preventing conduction of cold atmosphere and hot atmosphere from the environmental chamber to the torque meter.

7. The transmission testing device as claimed in claim 5, further comprising:
   a constant temperature chamber provided in the hollow of the spacer between the thermal insulation wall and the torque meter; and
   a temperature sensor disposed in the constant temperature chamber;
   wherein temperature of the constant temperature chamber is controlled based on a sensing signal from the temperature sensor.

8. The transmission testing device as claimed in claim 5, wherein the flange is provided with a thermal radiation flange at a shaft thereof, for preventing conduction of cold atmosphere and hot atmosphere from the environmental chamber to the torque meter through the flange.

9. The transmission testing device as claimed in claim 6, wherein:
   the thermal insulation wall is composed of separate parts; and
   the hole of the test product attachment holder is covered by an insulation plate after coupling between the test product and the flange.

10. The transmission testing device as claimed in claim 2, wherein the hollow of the test product attachment holder is connected to an air duct such that air is sent into the hollow through the air duct.

11. The transmission testing device as claimed in claim 6, further comprising:
- a constant temperature chamber provided in the hollow of the spacer between the thermal insulation wall and the torque meter; and
- a temperature sensor disposed in the constant temperature chamber;
- wherein temperature of the constant temperature chamber is controlled based on a sensing signal from the temperature sensor.

12. The transmission testing device as claimed in claim 6, wherein the flange is provided with a thermal radiation flange at a shaft thereof, for preventing conduction of cold atmosphere and hot atmosphere from the environmental chamber to the torque meter through the flange.

\* \* \* \* \*